United States Patent [19]

Ward, Jr.

[11] Patent Number: 4,861,830

[45] Date of Patent: * Aug. 29, 1989

[54] POLYMER SYSTEMS SUITABLE FOR BLOOD-CONTACTING SURFACES OF A BIOMEDICAL DEVICE, AND METHODS FOR FORMING

[75] Inventor: Robert S. Ward, Jr., Lafayette, Calif.

[73] Assignee: Th. Goldschmidt AG, Essen, Fed. Rep. of Germany

[*] Notice: The portion of the term of this patent subsequent to Jun. 23, 2004 has been disclaimed.

[21] Appl. No.: 65,416

[22] Filed: Jun. 22, 1987

Related U.S. Application Data

[63] Continuation of Ser. No. 507,517, Jun. 24, 1983, Pat. No. 4,675,361, which is a continuation-in-part of Ser. No. 385,813, Jun. 7, 1982, abandoned, and a continuation-in-part of Ser. No. 472,189, Mar. 4, 1983, abandoned, which is a continuation-in-part of Ser. No. 385,813, Jun. 7, 1982, abandoned, which is a continuation of Ser. No. 278,664, Jun. 29, 1981, abandoned, which is a continuation of Ser. No. 125,845, Feb. 29, 1980, abandoned.

[51] Int. Cl.$^4$ .................... C08L 75/00; C08L 83/10; C08L 83/12

[52] U.S. Cl. ...................... 525/92; 523/112; 523/113; 525/403; 525/424; 525/431; 525/440; 525/446; 525/453; 525/454; 525/457; 525/474

[58] Field of Search ............... 525/458, 453, 464, 474, 525/92, 403, 424, 431, 440; 523/112, 113

[56] References Cited

U.S. PATENT DOCUMENTS

| | | |
|---|---|---|
| 2,527,590 | 10/1950 | Speier, Jr. |
| 3,051,684 | 8/1962 | Morton et al. |
| 3,243,475 | 3/1966 | Reischl et al. |
| 3,246,048 | 4/1966 | Haluska |
| 3,296,190 | 1/1967 | Reischl et al. |
| 3,337,497 | 8/1967 | Bostick |
| 3,342,766 | 9/1967 | Huntington |
| 3,378,521 | 4/1968 | Bostick |
| 3,434,869 | 3/1969 | Davidson |
| 3,434,875 | 3/1969 | Smith et al. |
| 3,457,173 | 7/1969 | Pater |
| 3,562,352 | 2/1971 | Nyilas ............................... 128/214 |
| 3,576,904 | 4/1971 | Saam et al. |
| 3,600,418 | 8/1971 | Bailey et al. |
| 3,607,972 | 9/1971 | Kiles et al. |
| 3,640,943 | 2/1972 | Bostick et al. |
| 3,642,936 | 2/1972 | Hodge et al. ........................ 525/453 |
| 3,663,649 | 5/1972 | Wheeler, Jr. |
| 3,678,126 | 7/1972 | Saam et al. |
| 3,686,254 | 8/1972 | Morehouse |
| 3,691,257 | 9/1972 | Kendrick et al. |
| 3,701,815 | 10/1972 | Matzner et al. |
| 3,723,566 | 3/1973 | Thompson et al. |
| 3,798,185 | 3/1974 | Skiens et al. |
| 3,801,616 | 4/1974 | Litteral |
| 3,873,636 | 3/1975 | Saam et al. |
| 3,880,155 | 4/1975 | Rosoff |
| 3,890,405 | 6/1975 | Kendrick et al. |
| 3,903,882 | 9/1975 | Augurt |
| 3,928,490 | 12/1975 | Hergenrother |
| 3,933,407 | 1/1976 | Tu et al. |
| 3,961,122 | 6/1976 | Gaines et al. ..................... 525/90 |
| 3,975,455 | 8/1976 | Falender et al. |
| 4,137,360 | 1/1979 | Reischl |

FOREIGN PATENT DOCUMENTS

| | | |
|---|---|---|
| 6827765 | 6/1967 | Australia |
| 0068385 | 5/1983 | European Pat. Off. |
| 1944969 | 3/1970 | Fed. Rep. of Germany |
| 3107542A1 | 3/1982 | Fed. Rep. of Germany |
| 2318188 | of 0000 | France |
| 2399879 | 3/1979 | France |
| 62183 | 2/1985 | Israel |
| 26707198 | 10/1981 | Japan |
| 8100975 | 9/1981 | Netherlands |
| 811107 | 3/1982 | South Africa |
| 7010360 | 3/1982 | Taiwan |
| 1176490 | 1/1970 | United Kingdom |
| 1479344 | 7/1977 | United Kingdom |
| 1547311 | 6/1979 | United Kingdom |
| 1547834 | 6/1979 | United Kingdom |
| 2016482 | 9/1979 | United Kingdom |
| 2073219A | 10/1981 | United Kingdom |
| 2073219B | 2/1985 | United Kingdom |
| 2140437B | 6/1985 | United Kingdom |
| 2140438B | 6/1985 | United Kingdom |
| 2140444B | 6/1985 | United Kingdom |

OTHER PUBLICATIONS

Ward, R. L., et al., "Organometallic Polymers", *Acad. Press & Inc.*, C. E. Carkahek, ed., pp. 219–229 (1978).

Ward, R. L., "Development of Thermoplastics for Blood-Contacting Biomedical Devices", presented at 179th ACS National Meeting, Houston, Texas, 1980, *Coatings and Plastics Preprints*, 42, pp. 226–231 (approx. Mar. 9, 1980).

Brasch, J. L., "Hydrophobic Polymer Surfaces and Their Interactions With Blood", *Annals of the N.Y. Acad. of Sci.*, vol. 283, pp. 357–371 (1977).

LeGrand, D. G., et al., "Surface Activity of Block Copolymers of Dimethylsiloxane and Bisphenol-A Carbonate in Polycarbonate", *Polymer Preprint*, Amer. Chem. Soc., Div. of Polymer Chemistry, vol. 11, No. 2, pp. 442–446 (1970).

Dwight, D. W., et al., "ESCA Analysis of Polyphosphazene and Poly(Siloxane/Carbonate) Surfaces", *Polymer Preprint*, Amer. Chem. Soc., Division of Polymer Chemistry, vol. 20, No. 1, pp. 702–705 (1979).

Primary Examiner—Wilbert J. Briggs, Sr.
Attorney, Agent, or Firm—Flehr, Hohbach, Test, Albritton & Herbert

[57] ABSTRACT

A polymer admixture is formed from a base polymer and thermoplastic copolymer additive including polar hard segments and polar and nonpolar soft blocks in graft or block copolymer form. The polymer admixture is characterized by increased contact angle hysteresis and is formed into blood and tissue-contacting surfaces of a biomedical device or into textiles. A preferred additive comprises a segmented block copolymer having polydialkylsiloxanes as nonpolar soft blocks, and a polyurethane as hard segments and a polyalkylene oxide as a polar soft block.

61 Claims, No Drawings

POLYMER SYSTEMS SUITABLE FOR BLOOD-CONTACTING SURFACES OF A BIOMEDICAL DEVICE, AND METHODS FOR FORMING

This is a continuation of application Ser. No. 507,517 filed June 24, 1983, now U.S. Pat. No. 4,675,361, which is a continuation-in-part of Ser. No. 385,813, filed June 7, 1982, now abandoned, and a continuation-in-part of Ser. No. 472,189, filed Mar. 4, 1983, now abandoned, which is a continuation-in-part of Ser. No. 385,813, filed June 7, 1982 abandoned, which is a continuation of Ser. No. 278,664, filed June 29, 1981, now abandoned, which is a continuation of Ser. No 125,845, filed Feb. 29, 1980, now abandoned.

BACKGROUND OF THE INVENTION

The present invention is directed to methods of modifying surface properties of polymers with polymeric additives. Particularly, the invention is directed to methods of preparation and to polymers suitable for blood-contacting surfaces. The blood or tissue-contacting surfaces may be in the form of smooth surfaces or may be woven or knit. The present invention may also be applicable for preparing textiles having other specified surface properties, such as, oil resistance, water repellency and the like while also possessing launderability by virtue of the hydrophobic and hydrophilic groups of the polymeric additives and the additives surface activity.

Polysiloxanes are known to have a particularly low critical surface tension value and have been suggested for incorporation into polyurethanes to improve the surface characteristics of such materials. However, polysiloxane by itself is known to have a tendency to exude from the polyurethane base polymer as illustrated in Reischl et al U.S. Pat. No. 3,243,475.

Cross-linked, thermosetting polysiloxane-polyurethane block copolymers have been suggested for use as blood contact surfaces of biomedical devices as illustrated in Nyilas U.S. Pat. No. 3,562,352. The technique disclosed for such use includes fabricating the entire blood contact devices from such block copolymers or coating such devices with the copolymers. The block copolymers themselves may have poor structural characteristics due to a high proportion of polysiloxane. Furthermore, the coated materials are particularly expensive to form since they must be coated in a separate operation after the device is fabricated and are not processable by thermoplastic methods such as injection molding and extrusion. The manufacture of tubing, catheters and other blood-contacting disposable devices from such materials is particularly expensive due to the necessity of employing solution fabrication techniques.

Certain experimental work has been published relating to the blending of block copolymers of polydimethylsiloxane with other homopolymers. These materials are known to produce films with high siloxane surface concentrations. See, for example, D. G. Legrand and R. L. Gaines, Jr., Polym. Prepr. 11 442 (1970); D. W. Dwight et al, Polym. Prepr. 20, (1), 702 (1979); and J. J. O'Malley, Polym. Prepr. 18 (1977). However, these references do not describe the polymer blends as having characteristics which would be particularly advantageous in biomedical applications. In particular, silicone-containing polycarbonates have low contact angle hysteresis, a property, as discussed hereinbelow, which may render them unsuitable as a blood contact surface.

Minor amounts of block copolymers including segments of polydimethylsiloxane and homopolymers of polycarbonate, polystyrene, poly-(2,6-diphenyl-1,4-phenylene oxide), and polyamide-imide have been blended with base homopolymers for modifying the surface properties of the homopolymers. Gaines et al U.S. Pat. No. 3,961,122 suggests using such surface modified polymers as thin films, while Gaines et al U.S. Pat. No. 3,686,355 suggests a variety of uses including bulk uses. These patents, however, do not disclose polymer blends possessing the desired overall physical properties for biomedical applications of excellent flexibility and softness, while also possessing excellent strength.

SUMMARY OF THE INVENTION AND OBJECTS

It is the general object of the invention to provide a new form of polymer at low surface free energy and/or high contact angle hysteresis, particularly for use as the surface of a tissue or blood-contacting medical device, which is of low cost, is readily processed, and which is characterized by excellent engineering properties including flexibility, softness and strength. It is another object of the present invention to provide textiles and methods for preparing same by modifying surface properties of polymers with polymeric additives to form textiles having specified surface properties, such as, oil resistance, water repellency, launderability and the like.

Further objects and features of the invention will be apparent from the following description of its preferred embodiments.

One widely accepted hypothesis regarding blood compatibility is that it is maximized within a narrow range of surface free energies, which give rise to favorable interactions with plasma proteins. A common measurement of surface free energy is by Zisman's critical surface tension, $\gamma_c$. The optimum value has been found empirically to lie within the range of about 20 to 30 dynes per centimeter. See Baeir, Ann. N.Y. Acad. Sci., 17, 282 (1967).

Many common polymers, which are used for blood-contacting biomedical devices and which provide the desired mechanical properties, often do not fall within this range of critical surface tension. Other polymers, however, possess critical surface tensions which do lie within the proposed optimum range, but do not exhibit good blood compatibility. Polyethylene, for instance, is one polymer whose critical surface tension lies in the middle of the range, in that it has a critical surface tension of 25 dynes/cm, but is not considered to be particularly compatible with blood.

A large number of polymer compounds which are useful in blood contacting and tissue contacting biomedical devices have critical surface tensions within the 20 to 30 dyne per centimeter range because they contain certain impurities or processing aids, which have been admixed with the polymer to give the desired processability or physical properties. However, these materials, despite having critical surface tensions in the optimum range of 20 to 30 dynes/cm identified by Baier, ibid., do not exhibit good blood compatibility. They tend to adsorb formed elements of the blood, such as platelets. These formed elements aggregate into blood clots, which remain adherent to the surface of these polymers, or which leave the surface as aggregates or emboli under the forces of flowing blood. These aggregates, or emboli may end up lodged in capillary beds downstream of the site of implantation. These capillary beds often are within vital organs and their blockage by emboli can cause substantial morbidity to the patient, whose blood is contacting the implant, or device.

While many apparently blood-compatible materials do have critical surface tensions which lie within the optimum range as proposed by Baeir, ibid., it appears that some other property of the surface besides the critical surface tension may be responsible for the blood compatibility of some polymers and the lack of blood compatibility of others. The surface quantity which may account for blood compatibility is one which is related to the adaptability of the surface to minimize interfacial energy with its environment. A surface with this ability to reorient its chemical groups and thus minimize interfacial energy with the phase with which it is in contact, will be blood compatible because when it is immersed in blood, it will reorient to minimize interfacial energy with the blood. Plasma proteins, which then adsorb onto this polymer surface will be subjected to a considerably lower energy gradient between the surface and their normal environment, the blood. Under these conditions, it is believed that the plasma proteins will become relatively less denatured or changed in their structure relative to the structure they have in free-flowing blood, and that because of this relatively lower degree of denaturation, will induce relatively less thrombosis.

It is well-known that the first step in surface-induced thrombosis involves the adsorption of plasma proteins onto a surface. Once adsorbed on the surface, or in the act of adsorbing onto the surface, the proteins may become denatured. A related effect is that the composition of the adsorbed plasma protein layer may vary depending upon the chemistry of the blood contacting surface. These effects may induce varying reactions certain of which eventually cause aggregation of platelets and the formation of thrombus on the surface.

Therefore, it can be said that the "right" chemistry for a surface to possess in contact with blood is one that will adsorb the desirable proteins. Albumin has been identified as one of these desirable proteins.

Alternatively, the type of surface chemistry that is desirable for the blood contact surface to possess may be considered to be one upon which proteins will adsorb and then denature only to a degree which will not induce the subsequent reactions which eventually lead to aggregation of platelets and thrombus formation.

It is believed that a quantity which reflects the ability of a surface to reorient its surface chemical groups to minimize interfacial energy, is the quantity called contact angle hysteresis. This quantity is measured by determining the angle of contact of a small droplet of the solvent of interest on the surface, for example, water, first as it advances over the surface for the first time and then as it recedes from the same surface over which it has just advanced.

The results of the contact angle hysteresis measurement may be presented using the quantity relative contact angle hysteresis, which is the advancing angle minus the receding angle all divided by the advancing angle. See F. J. Holly, *Organic Coatings and Plastics Chemistry*, vol. 45, Am. Chem. Society Monograph (1981), p. 796. Using this criteria, the best smooth blood contacting surfaces will have the highest contact angle hysteresis, that is, when they first come in contact with the solvent of interest, for instance water, they will look very non-polar because they have been in contact with air prior to this water contact. But as the drop recedes over the same smooth surface, the angle measured is that which exists between the reoriented surface and the solvent, and here the receding angle will be much less than the advancing angle indicating that the surface has reoriented to minimize interfacial tension and increase wetability by the solvent.

Therefore, it is an object of the present invention to provide a method for increasing the relative contact angle hysteresis of bulk polymers by use of thermoplastic segmented block copolymer additives.

In accordance with the above, a novel technique has been provided for forming a novel class of polymer admixtures, particularly suitable for use as the exposed blood-contacting surface of a biomedical device or component. In one embodiment, a minor amount of a polymer additive, such as a thermoplastic segmented block copolymer, is dispersed through a base polymer while both are fluid to form a polymer admixture. The additive includes at least two different polymer components preferably in a block or graft copolymer form. These two polymer components form at least one chain, hereinafter referred to as the first chain. The first chain may be an essentially linear segmented copolymer characterized by the presence of at least one polar (relatively hydrophilic) hard segment (preferably a homopolymer) having a glass transition temperature (Tg) or crystalline melting temperature (Tm) above body temperature (about 37° C.), and at least one nonpolar (relatively hydrophobic) soft block (preferably also a homopolymer, such as, a polysiloxane) having a glass transition temperature or crystalline melting temperature below body temperature (about 37° C.). The nonpolar soft block is of low surface free energy, while the hard segment is characterized by an ability to reduce the tendency of the soft block to exude from the base polymer. Optionally, another chain may be present in the additive, hereinafter referred to as the second chain, which is chemically bonded to the first chain, and may be either a polar homopolymer characterized by a Tg or Tm below body temperature (about 37° C.), or a second essentially linear segmented copolymer characterized by the presence of at least one polar hard segment (preferably a homopolymer) and at least one polar soft block (preferably a homopolymer) having, respectively, a Tg or Tm for a soft block as described hereinabove. Preferably, the polar soft block in the second chain may be polyvinylpyrrolidone, polyethylene oxide and the like. Preferably, the base polymer and one of the hard segments are at least partially compatible (e.g., polyurethane). The hard segments of the first and second chains have the dual purpose of giving the additive physical properties such that structural strength of the admixture of additive and base polymer is not significantly reduced with respect to the structural strength of the base polymer, and of reducing the tendency of the additive to exude from the base polymer. Thermodynamic compatibility of the additive and the base polymer are not necessary. A high degree of compatibility, in fact, can reduce the tendency of the additive to be surface active. Such additives will be less efficient as a surface-modifier than those containing hard segments of lower compatibility with the base polymer.

DETAILED DESCRIPTION OF THE PREFERRED EMBODIMENTS

One major feature of the present invention is to provide a technique for increasing the contact angle hysteresis and/or reducing the critical surface tension (a measure of surface free energy) of a structural polymer to provide a blood or tissue compatible surface and further to provide a method of making a structural polymer more adaptable to its environment. A particularly advantageous feature according to the present invention is to provide a method whereby one may controllably vary the balance of the polar(hydrophilic) to the nonpolar(hydrophobic) groups on the surface of a polymer by use of an additive. Moreover, the surface polar-nonpolar group balance may be varied according to the present invention independently of the base polymer.

As used herein, the term "base polymer" will refer to the polymer whose surface characteristics are so modified. Such base polymers often have excellent physical properties, such as being characterized by high flexibility, e.g., a flexural modulus below 80,000 psi, good softness, e.g., a hardness of less than M60 on the Rockwell M scale; a glass transition temperature or crystalline melting temperature below 140° C.; and good structural strength, e.g., a tensile strength greater than 2500 psi. It is understood that when the modified base polymer is to be formed into fibers for use in woven textiles, that the flexural modulus may be above 80,000 since fibers will be inherently flexible enough for such uses. Chemically, such base polymers fall into the class of segmented or block copolymers, blends thereof, or in the class of thermoplastic homopolymers, or homopolymer mixtures, which may also contain plasticizing agents. Plasticized polyvinyl chloride and polyethylene, for example, may be used as base polymers.

Typical base polymers whose surfaces may be improved by the present technique include polyurethanes, polysulfones, polycarbonates, polyesters, polyethylene, polypropylene, polystyrene, poly(acrylonitrile-butadienestyrene), polybutadiene, polyisoprene, styrene-butadiene-styrene block copolymers, styrene-isoprene-styrene block copolymers, poly-4-methylpentene, polyisobutylene, polymethyl-methacrylate, polyvinylacetate, polyacrylonitrile, polyvinyl chloride, polyethylene terephthalate, cellulose and its esters and derivatives, and the like.

The term "segmented" refers to the relatively short length of a repeating unit, e.g., less than about 10 monomeric units, but preferably less than three monomeric units, typically alternating more than once, with structural formulas such as ABAB. The segmented block copolymers in the first and second chains of the additive have at least one hard segment chemically bonded to at least one soft block. They may include more than one hard segment or soft block of the same or different chemical nature, so long as all blocks and segments are coupled by covalent linkages. The hard segments of the first and second chains are relatively short in length, typically including from 1 to 10 repeating units and are characterized by a crystalline melting point ($T_m$) or glass transition temperature ($T_g$) greater than their use temperature. The hard segments must be short in length relative to the nonpolar and polar soft blocks in order for the additive to increase contact angle hysteresis and blood compatibility of the base polymer. For use in contact with blood in the human body (temperature 37° C.), the $T_g$ or $T_m$ value of the hard segments are above that temperature. If the soft block having a $T_g$ or $T_m$ below the use temperature of 37° C. for blood contact were to be in the form of homopolymers, they would be liquid-like at that temperature. However, the overall segmented block copolymer comprising the first and second chains is rigid because of the presence of the hard segments. Such segmented block copolymers are characterized by two-phase micromorphology due to the thermodynamic incompatibility of the soft blocks and hard segments. Suitable nonpolar soft blocks include 5 to 300 repeating units and a molecular weight of 200 to 20,000. The polar urethane hard segments typically include 1 to 10 preferably less than 3 repeating units and a molecular weight of 300 to 3000 but are short in length relative to the soft blocks. The segmented polyurethanes may preferably be the reaction products of polymeric ether glycols and a slight excess of diisocyanate, and a chain extending diamine or dihydroxy derivative. By the use of various types of isocyanates (e.g., aliphatic or aromatic), glycols (e.g., polyethylene, polypropylene, or polytetramethylene oxides) and chain extenders (aliphatic or aromatic), the structural properties may be varied depending upon the end use of the material. As used herein, the term "segmented polyurethane" includes, but is not limited to, polyether urethane ureas, polyether urethanes and polyester urethanes.

While segmented polyurethanes are highly effective base polymers for use in the present invention, other segmented or block copolymers with similar structural properties may also be used, e.g., polyester-polyethers, polyesters (e.g. Dacron), polyether-polyamides, polyamides (e.g. nylon), styrene-isoprenes, styrene butadienes, thermoplastic polyolefins, styrene-saturated olefins, polyester-polyester, ethylene-vinyl acetate, ethylene-ethyl acrylate, ionomers, thermoplastic polydienes. Also, reinforced rubbers may be used wherein the reinforcement serves the same purpose as the hard block in the segmented copolymer.

The base polymer is of a type capable of being formed into a self-supporting structural body, a self-supporting film, deposited as a coating onto a self-supporting body, or woven or knit as a fiber. A particularly effective end use of the final product is the surface of a biomedical device or component. The base polymer may be a thermoplastic material which is no more than partially thermodynamically compatible with the additive. The base polymer may be a copolymer, a pure homopolymer, or a homopolymer mixed with plasticizers.

For biomedical applications, other characteristics of the base polymer are that it usually exhibits a critical surface tension ($\gamma_c$) in excess of that desirable for a blood contact surface and in excess of the polymer additive, and/or exhibits a contact angle hysteresis lower than desirable for a blood contact surface. As defined herein, $\gamma_c$ measurements are performed by the direct method using a contact angle meter of the Kernco or Rame-Hart type and a series of seven solvents according to the Zisman procedure as set forth in A. W. Adamson, *Physical Chemistry for Surfaces*, 339–357, 351 (3d Ed.). Measurements are made at room temperature using advancing angles on microscopically smooth solvent cast films annealed at 60° C. for at least four hours. The mean contact angles are fitted to a Zisman plot using a linear regression calculator program. The contact angle hysteresis measurements were made by the method set forth in Adamson, ibid., pp. 347-348.

In accordance with the present invention, a base polymer of the foregoing type is mixed with a polymer additive to lower its surface free energy, to increase its contact angle hysteresis and, in certain instances, to improve structural properties of the base polymer. The polymer additive, with a substantially lower $\gamma_c$ value than that of the base polymer, is thoroughly dispersed into the base polymer while in fluid form to form a fluid polymer admixture. The additives must be thermoplastic, fusible material soluble in a solvent and relatively uncrosslinked. Thereafter, the polymer admixture is solidified and formed into the blood-contacting surface of a biomedical device or component. A suitable broad range of surface free energies of the polymer admixture is from 10 to 35 dyne/cm., preferably less than 30 dyne/cm. An optimum range is 20-25 dyne/cm.

The polymer additive includes at least two different polymer components (preferably each are homopolymers) which form at least one essentially linear segmented copolymer chain, the chain comprising at least one polar hard segment (preferably a homopolymer) and one nonpolar soft block (preferably also a homopolymer). The purpose of the polymer additive in the base polymer is to lower the critical surface tension of the base polymer-polymer additive admixture and to also increase the contact angle hysteresis. The nonpolar soft block has a relatively low $\gamma_c$ value, less than that of both the base polymer and the hard segment and thereby imparts a surface activity to the additive. Presence of the additive with a relatively low $\gamma_c$ causes reduction in the $\gamma_c$ of the polymer admixture. To prevent exudation from the base polymer of the soft block, the hard segment is chemically bonded to the soft block in the polymer additive thereby increasing rigidity. Another function of the nonpolar soft block is to modify and control the surface properties of the polymer admixture.

For biomedical applications, the polar hard segment of the first chain is characterized by a crystalline melting point greater than about 37° C. and/or a glass transition temperature also greater than about 37° C. This polar hard segment has a higher surface free energy than the nonpolar soft block of the first chain.

The polymer additive may also comprise a second polymer chain ("second chain") which is chemically bonded to the copolymer chain ("first chain"). Such polymer additives are referred to as segmented block terpolymers or segmented block multipolymers. The second polymer chain is selected from a polar homopolymer or a second segmented essentially linear copolymer. The second segmented copolymer is characterized by at least one polar hard segment (preferably a homopolymer) and one polar soft block (preferably also a homopolymer). The polar hard segments of both the first and second chains have a glass transition temperature or crystalline melting temperature above 37° C. The polar and nonpolar soft blocks have a glass transition temperature or crystalline melting temperature below 37° C. The purpose of the second polymer chain is to provide easily orientable polar groups so that when in contact with a fluid environment a sufficient number of polar groups may be directed to the surface of polymer admixture so that the surface becomes more compatible with the polarity of the fluid, thereby increasing the value of the contact angle hysteresis between the liquid and polymer surface. The second chain is thereby a means by which the surface properties of the polymer admixture may be modified and controlled.

It has been found that in the polymers according to the present invention the polymer component of the additive with the lowest $\gamma_c$ value controls the $\gamma_c$ value of the entire polymer additive when annealed in warm air to achieve surface equilibration. Thus, for example, if the soft blocks have a $\gamma_c$ value of 25 and the hard segments have a $\gamma_c$ value of 35, the total $\gamma_c$ of the air annealed additive is approximately 25. Furthermore we have found that to be surface active in a particular base polymer the segmented copolymer additive must contain at least one soft nonpolar block having a (critical) surface tension lower than the base polymer. The criteria of thermodynamic incompatibility alone is not enough to insure surface activity of block in a base polymer.

For biomedical applications, suitable polymers for the soft blocks of the first chain are those which give $\gamma_c$ values lower than that of the value of the base polymer and thus causing the additive to be surface active in the base polymer. Thus, it is preferable that such soft blocks be characterized by a $\gamma_c$ value less than about 30 dyne/cm. One particularly effective polymer for this purpose is a polydimethysiloxane with a $\gamma_c$ on the order of 22 dyne/cm. Techniques for forming siloxane copolymers for use in the present invention are known, e.g., as described in W. Noll, *Chemistry and Technology of Silicones* (Academic Press, 1968), the disclosure of which is incorporated by reference herein. Other suitable nonpolar soft block component polymers include other polydialkylsiloxanes, polyfluoroalkyl alkylsiloxanes, polyalkylene oxides, polyolefins, polydienes and polyfluorocarbons.

Preferably the polar hard segment of first chain of the additive may have a repeat unit of about 1 to 10. Most preferably, the repeat unit will be about 1 or 2. The repeat unit for the nonpolar soft block of the first chain may be greater than about 5, preferably about 20 to 50.

If the second chain is a segmented block copolymer, the repeat unit for the polar hard segment may be about 1 to 10, preferably about 1 or 2. The repeat unit for the polar soft block may be greater than about 5, preferably about 20 to 50. If the second chain is a homopolymer as described herein, the repeat unit preferably has a molecular weight from about 200 to about 10,000.

Thus, preferred additives according to the present invention may be described as block polymers including a sequence of block segments represented by the formula [A][B][C][D] in which A is a polar hard segment of the first chain with a crystalline melting point or glass transition temperature above 37° C., B is a nonpolar soft block, for example, poly(dialkylsiloxane) C is a polar hard segment of the second chain with a crystalline melting point or glass transition temperature above 37° C., and D is a polar soft block of the second chain with a crystalline melting point or glass transition temperature below 37° C., selected from the group consisting of polyalkylene oxide, and polyalkylene oxidecopolyalkylene oxide, polyvinylalkanoates, e.g., polyvinylacetate and the like, or C and D together form a polar homopolymer having a glass transition temperature or crystalline melting point below 37° C. selected from the group consisting of polyalkylene oxide, polyalkylene oxidecopolyalkylene oxide, and polyvinylalkanoates, e.g., polyvinylacetate, polyvinylpropionate, and the like. The polymer additive as a whole will be essentially water insoluble.

The components A and B may be a copolymer, as may be C and D, i.e., the additive may be of the formula ([A][B])$_n$—([C][D])$_m$ wherein n and m are positive integers and A, B, C and D are as described above.

The hard segments A and C in the formula above may be identical. Also C may be absent, whereby the second chain will comprise the homopolymer D. Alternatively, in the absence of C, B and D together may be a soft block copolymer with both polar and nonpolar blocks whereby the additive will be of the formula [A]([B][D])$_p$, wherein p is a positive integer. A preferred soft block copolymer (B)(D) is a polydimethylsiloxane oligomer having polyethylene oxide terminal groups.

Where the polymer admixture of the present invention is formed by mixing a preformed polymer additive of the foregoing types with a base polymer, such polymer additive is suitably formed of block copolymers of alternating hard segment and soft block components interlinked by chemical bonds in accordance with known techniques. For example, such block copolymers may be formed in accordance with the Noshay and McGrath, *Block Copolymers Overview and Critical Survey*, (Academic Press 1977), the disclosure of which is incorporated herein by reference. A suitable number of repeating units of each polymer of the polar and nonpolar soft block component is that sufficient to retain the approximate $\gamma_c$ value of the polymer as evidenced by retention of approximately the same glass transition temperature as its pure homopolymer. Typically, this number is on the order of 5 to 10 units or more. Similarly, there should be a sufficient number of repeating units of the hard segment so that the polymer additive is rigid at room temperature. The respective hard segments of the first and second chain may be the same or different. The polar soft block component of the second chain, if present, will be different from the nonpolar soft block segment of the first chain.

The preparation of segmented block copolymers (or multipolymers) may be performed by several procedures which differ in the degree to which the structure of the resulting product may be defined.

One procedure involves the coupling of two (or more) preformed blocks or segments which are prepared in separate reactions prior to the coupling reaction. This procedure involves a well defined structure if the coupling reaction precludes like blocks or segments from reacting with themselves but only allows dissimilar blocks or segments to couple to one another.

Other coupling reactions may occur resulting in a less defined structure if the two preformed blocks or segments possess the ability (via the coupling reaction) to react with themselves as well as the dissimilar block or segment.

Additional coupling reactions may occur when a single (or more) preformed block or segment is coupled with a second block or segment created during the coupling reaction. In this case the initial length of the preformed block or segment is known (by virtue of the separate reaction used to prepare it) but the sequence distribution of the copolymer is not known exactly since both coupling and chain growth is possible in the reaction which produces the second block or segment. Suitable methods of forming these and other such copolymers for use in the present invention are set out in the aforementioned Noshay and McGrath publication.

One particularly preferred admixture according to the present invention includes a block copolymer of poly(dialkylsiloxane), specifically poly(dimethylsiloxane), as the nonpolar soft block component for the first chain, a polyether or polyester as the polar soft block component of the second chain and a non-segmented polyurethane as the hard segment component for both the first and second chains. As used herein, the term "polyurethane" encompasses polyether urethaneureas polyether urethanes, polyester urethanes, or any of the other known polyurethanes. The hard segment component may be a polyurethane reaction product of diisocyanate/diol diamine hydrazine or water. This copolymer may be blended with a base polymer of desired physical properties.

Another preferred additive includes the terpolymer wherein the second chain is a polymer wherein either polyethylene oxide or polyethylene oxide-copolypropylene oxide (hydrophilic component) is chemically bonded to polyurethane segments. In this instance, the second chain comprises a polar hard segment with a crystalline melting point above 37° C. or a glass transition temperature above 37° C. In this instance the additive comprises the hard segments and soft blocks of the first chain and the polar polymeric second chain. In one excellent terpolymer, the nonpolar soft block component is a poly(dialkylsiloxane), the polar hard segment component is any of a broad group including polyurethane or polyureaurethane, and the polar polymer is as described above.

Particularly, we have found that additives comprising terpolymers of polyurethane/polyethyleneglycol/polydimethylsiloxane perform well. These additives possess the very non-polar polydimethylsiloxane groups and the very polar polyethylene oxide groups, both of which may be used at a molecular weight that causes them to be above their glass transition temperatures and/or melting points at the use temperature of 37° C. The presence of both polar groups and non-polar groups in the additive is important for blood compatibility, but these groups should also be mobile enough at body temperature (or other temperatures at which they are used) in order to reorient or exchange places with one another according to the environment in which the surface is immersed. Materials which possess both polar and non-polar components, but which are glassy or crystalline at use temperature and therefore not able to reorient quickly may be ineffective in producing the desired properties of the blood contacting surface.

Other forms of polymers are of the graft copolymer type. Either the first or second chain may serve as the substrate upon which the pendant chains of tee other type of polymer are grafted. The mode of forming graft copolymers is well known to those skilled in the polymer field. For example, see pp. 13–23 of the aforementioned Noshay and McGrath publication. The third mechanism in Table 2-1 of Noshay and McGrath illustrates a backbone structure suitable for grafting a hydroxyalkyl-terminated polydimethylsiooxane (e.g., through a urethane linkage using a diisocyanate).

The ratio of total hard segments and total soft blocks in the polymer additive may vary to a considerable extent so long as there is sufficient amount of total soft blocks to reduce the $\gamma_c$ value and sufficient amount of total hard segments to prevent exudation of the polymer additive. It is preferable that the polymer additive include at least bout 20 volume % of total soft block component. A suitable ratio is from 20 to 80 volume % of total soft block component and about 80 to 20 volume % of total hard segments of polymer component. When the second chain is a homopolymer, it will be considered a soft block component when calculating these ratios.

Referring to modified surface properties, the total amount of polymer additive required to reduce the $\gamma_c$ value of the base polymer to that desired for the polymer admixture is very low. For example, it has been found that less than 5 volume % and preferably less than 1 to 2 volume % of total soft block component based on the polymer admixture performs this function even though the soft block component typically comprises about half or less of the polymer additive. A suitable ratio of total soft block component to base polymers is up to 2 volume % based on the total polymer admixture. Although the polymer additive is initially mixed and blended in bulk into the base polymer, it migrates to the surface to form an exceptionally thin (possibly monomolecular) film which provides the desired surface characteristics. Sufficient polymer additive should be included to provide this uniform layer.

The presence of an adequate amount of polymer additive is shown by a dramatic drop in the $\gamma_c$ value of the polymer admixture to approximately that of the soft block component having the lowest $\gamma_c$. While the required amount varies from system to system, in many applications it is less than 1 volume % of the total soft block component based on the total polymer admixture.

The minimum amount of polymer additive to provide the above modified surface properties may be approximated by a knowledge of the film thickness of a polymer additive monolayer and the surface area-to-bulk volume ratio of the fabricated material, e.g., its physical dimensions. This is based on the simplifying assumption that prior to surface saturation, essentially all of the polymer additive migrates to the surface. By simple calculation, this minimum amount may be precalculated based on this knowledge.

Referring to modified bulk properties, in another embodiment of the invention, polymer additives of the foregoing type are thoroughly blended with base polymers of the foregoing type to modify not only surface properties but also bulk properties of the base polymer. The total proportion of the total soft block component may be increased substantially from that level set forth for modifying only surface properties. For example, a minimum of 5 volume % of the soft block component in the total polymer admixture, to as high as 50%, may be called to modify certain bulk properties of the admixture without adversely affecting other bulk properties. For example, the addition to a polyurethane base polymer of 20% of an additive comprising a block copolymer of 50% polydimethylsiloxane and 50% polyurethane, reduces Shore hardness (a measure of indentation hardness) of the admixture (by 11%) without adversely affecting the polymer strength. The amount of total soft block component is determined by its percentage in the additive and the percentage of the additive in the base polymer. The precise amount will vary depending upon the desired bulk properties and the particular polymer system. For biomedical applications such as heart pumps, the Shore hardness of the polymer admixture is important. A reduction of at least 5 shore units (A or D scale) hardness is significant. A range of 5 volume % to 20 volume % soft block component has been found to be suitable for this purpose without adversely affecting strength. A comparison of certain bulk properties of a polyurethane base polymer as a function of volume % of polydimethylsiloxane is set forth in the table below.

From the table it may be seen that silicone modified polymers all exhibit a hardness of at least 5 shore units lower than the unmodified base polymer.

A number of techniques may be employed for mixing the polymer additive with the base polymer in accordance with the present invention. In one technique, both the base polymer and polymer additive are thermoplastic and are melted at elevated temperatures to perform the mixing. Thereafter, the polymer is solidified by cooling. If desired the bulk polymer may be simultaneously

| PROPERTIES OF THERMOPLASTIC ELASTOMERS | | | | | | | |
|---|---|---|---|---|---|---|---|
| TEST | TEST METHOD | UNITS % | | | | | |
| Silicone Content[2] (nom) | | | 0.0 | 5.0 | 10.0 | 20.0 |
| Indentation Hardness | ASTM D-2240 | Durometer A | 85 | 77 | 76 | 74 |
| Young's Modulus | (TMA)[1] | lb/in$^2$ | 1942 | 1844 | 1982 | 1765 |
| Tensile Strength | ASTM D-1708 | lb/in$^2$ | 5193 | 5191 | 4452 | 3478 |
| Ultimate Elongation | ASTM D-1708 | % | 659 | 698 | 691 | 681 |
| Tensile Stress At | ASTM D-1708 | lb/in$^2$ | | | | |
| 50% Elongation | | | 534 | 917 | 823 | 415 |
| 100% Elongation | | | 654 | 1222 | 1152 | 594 |
| 300% Elongation | | | 1248 | 2445 | 2139 | 1128 |
| Optical Clarity | | TRANSPARENT | | | | |
| Critical Surface Tension, $\gamma_c$ | | dyne/cm | 30 | 20 | 20 | 20 |

[1] Test Method: Perkin-Elmer Thermal Analysis Application Study 20, Polymer Testing by TMA by Bruce Cassel (1977).
[2] Remainder of elastomer is a polyurethane polymer formed from polytetramethylene oxide/methane bis(4-phenyl-)isocyanate/1,4-butanediol.

processed into the desired final form. Alternatively, the material may be solidified for subsequent formation of the material into the desired form by thermoplastic methods such as injection molding and extrusion.

Another technique for mixing of the polymer additive and base polymer is by dissolving both of them in solvent and thereafter evaporating the solvent simultaneous with fabrication or coagulating in a nonsolvent to form the solid product of the present invention. This product may also be subsequently processed by thermoplastic techniques if desired.

A third technique for forming the polymer admixture of the present invention is to polymerize in place with a vast excess (e.g., at least 95 volume %) of base monomer and a minor amount (e.g., no greater than 5 volume %) of a polymer additive of the soft block component type set out above. For example, low molecular weight polydimethylsiloxane having hydroxyalkyl end groups is substituted for a small amount of polyetherglycol in the synthesis of a typical polyether urethane. In such a case, the reaction product may contain enough silicon/polyurethane block copolymer to provide the desired surface characteristics. The concentration of the polymer additive would be so low that the great majority (e.g., at least 95 volume %) of the base polymer would not be linked to the additive polymer.

The polymer additive of the present invention must be thoroughly dispersed in the base polymer. For this purpose, it is necessary that at the time of mixing the base polymer be thermoplastic, soluble in organic solvents, and relatively uncrosslinked.

For most biomedical applications, the base polymers of the present invention should be thermoplastic so that they may be readily processed as desired. However, there are certain applications in which the polymers may be fabricated while fluid and thereafter solidified in the form of the fabricated part which cannot again be placed into the fluid form. For example, such base polymer may comprise thermosetting systems which are cured or vulcanized immediately following dispersion of the polymer additive. The base polymer may also comprise systems containing one or more components which are curable by the same or different curing agents. For example, the base polymer may contain one or more components which are vulcanizable by free-radical cross-linkers, such as peroxides, and also contain one or more components which are curable by a different agent, such as a borohydride. Such systems may include two component polyurethanes or epoxy resin systems. Also, the base polymers may be thermoplastic homopolymers containing plasticizers. A preferred homopolymer base polymer is polyvinyl chloride containing plasticizers.

One advantageous system in accordance with the present invention comprises an admixture of a polymer additive formed of a poly(dialkylsiloxane) segment chemically bonded to a polyurethane segment (e.g., in a block or graft copolymer) and admixed with a suitable base polymer, e.g., the same type of polyurethane as in the copolymer. A particularly effective system for modifying surface properties includes a polymer additive comprising a block copolymer of about 50 weight % polydimethylsiloxane and 50 weight % polyurethane (specifically polyester urethane). A suitable ratio is 99.9% polyester urethane base polymer and 0.1% of the block copolymer.

One mode of pretreating a base polymer to lower its surface free energy is believed to be effective with a base polymer which includes high energy end groups, specifically ones capable of hydrogen bonding or reacting with protein. In this instance, the base polymer is first fractionated to remove a lower molecular weight fraction and thereby may reduce the hydrogen bonding capacity of the remaining base polymer. Suitable techniques for accomplishing this are set out in Manfred J. R. Cantow, *Polymer Fractionation*, Academic Press (New York London 1967). Such techniques include liquid chromatography, particularly gel permeation chromatography, fractional precipitation or fractional dissolution.

It has been found that variations in processing conditions which would otherwise affect the surface free energy to a significant extent may be minimized as a factor in systems of the present invention by the use of a short heat treatment following surface formation. For example, in a system comprising a base polymer of polyether urethane and a block copolymer of polyether urethane/polyalkylsiloxane, annealing for four hours at 75° C. yields a $\gamma_c$ value approximately equal to that of pure polsiloxane while it takes a considerably longer period of time to accomplish this objective at room temperature.

It has further been found that the polarity of the environment of formation affects the initial $\gamma_c$ value of the surface. Thus an air equilibrated surface provides a lower $\gamma_c$ than one which has been equilibrated in water.

The polymer admixtures of the present invention are particularly effective for use as a blood-contacting surface of a biomedical device or component. Such devices include auxiliary ventricles, intraaortic balloons, and various types of blood pumps and vascular prostheses.

A further disclosure of the nature of the present invention is provided by the following specific examples of the practice of the invention. It should be understood that the data disclosed serve only as examples and are not intended to limit the scope of the invention.

EXAMPLE 1

A typical synthesis of Polydimethylsiloxane Polyurethane Block Copolymer.

To a 500 ml. four necked equipped with stirrer, Dean and Stark trap, dropping funnel, drying tube, thermometer and inert gas inlet is place a mixture of 50 ml. dimethylformamide and 140 ml. of tetrahydrofuran. The mixture is heated to reflux and approximately 40 ml. tetrahydrofuran is distilled off. The reaction mixture is cooled down and 12.513 gm (0.05 mole) of methane bis(4-phenyl) isocyanate (MDI) is added to give a clear solution. From the dropping funnel 15.000 gm. (0.015 mole) of 3-hydroxypropyl terminated polydimethylsiloxane (Mol. wt. approx. 1,000) is added dropwise. The reaction mixture is heated at 105° C. for 1 hour, followed by dropwise addition of 3.15 gm (0.035 mole) of 1,4-butane diol over a period of 45 minutes. The polymerization is carried out for 15 minutes more, cooled down and precipitated by pouring into water in a blender. The slightly yellowish polymer is washed with water and finally with ethanol; dried in a vacuum oven at 50° C. to afford approximately 30–31 gm of polymer (97–100%). Intrinsic viscosity [$\eta$] in tetrahydrofuran at 25° C. is 0.19.

EXAMPLE 2

By replacing some of the hydroxypropyl terminated polydimethylsiloxane with polyethylene glycol, a polydimethylsiloxane/polyethylene oxide/polyurethane terpolymer is prepared.

EXAMPLE 3

By replacing the DMF solvent with dimethylacetamide and substituting ethylene diamine for butane diol in Example 2, a polydimethylsiloxane/polyethylene oxide/polyureaurethane terpolymer is prepared.

EXAMPLE 4

This example illustrates solution fabrication. A solution is prepared containing about 10 weight % admixture in a solvent system consisting of 90% tetrahydrofuran (vol/vol) and 10% dimethylformamide. The admixture consists of 99.0 weight % purified polyesterurethane and 0.1 weight % silicone/polyurethane block copolymer. The block copolymer consists of about 50 weight % of polydimethylsiloxane and 50 weight % polyurethane from diphenylmethane diisocyanate and butane diol.

The solution is coated onto tapered stainless steel mandrels by multiple dipping. The solvent is allowed to evaporate and the film is removed from the mandrel.

The resulting "balloon" is mounted on a predrilled catheter and is useful as a cardiac arrest device when placed in the descending aorta and inflated and deflated with $CO_2$ in counterpulsation to the heart.

The $\gamma_c$ of the balloon film is 20 to 22 dyne/cm. Results of animal testing showed that this balloon had less thrombus on the balloon film and less emboli in the kidneys than was found with commercially available balloons (Datascope and AVCO).

EXAMPLE 5

Small test tubes are coated on their inner surface with two different polymer solutions (in THF) at 10 weight % concentration. One solution consists of polyetherurethane in the solvent. The second solution consists of 90 weight % solvent, 9.9 weight % polyetherurethane and 0.1 weight % copolymer additive. The soft block of the copolymer consists of about 50% polydimethylsiloxane and 50% polyethylene oxide copolypropylene oxide coupled together with an aromatic urethane hard segment of MDI (diphenylmethane diisocyanate) and butane diol. After solvent evaporation and about 16 hours equilibration in normal saline, fresh whole blood is placed in three tubes of each type.

Tubes coated with the unmodified polyetherurethane give a mean whole blood clotting time of 47.8 minutes. Tubes coated with polyetherurethane containing the block copolymer additive give a mean whole blood clotting time of 76.2 minutes. Uncoated glass control gives a mean clotting time of 11.8 minutes.

The $\gamma_c$ of the unmodified polyetherurethane is about 28 dyne/cm. The $\gamma_c$ of the polyetherurethane containing the block copolymer additive is about 20 dyne/cm. It remains free of thrombus when implanted in a calf.

EXAMPLE 6

This example illustrates thermoplastic fabrication.

A thermoplastic polyurethane is mixed in a twin screw extruder at about 400° F. with a block copolymer additive consisting of about 50 weight % polydimethylsiloxane and 50 weight % polyetherurethane such that the total silicone concentration of the mixture is 0.1 weight %. The admixture is extruded into the shape of tubing suitable for the transfer of blood. The tubing has a $\gamma_c$ of about 21 dyne/cm after being annealed at 60° C. for six hours.

EXAMPLE 7

This example illustrates two component vulcanizing. DuPont Adiprene L167 polyetherurethane isocyanate terminated prepolymer is prepared according to the manufacturer's recommendations for a polyol cure, using a slight stoichiometric deficiency of butane diol/trimethylol propane mixture. While still liquid 0.1 weight % of the previous dried block copolymer additive of Example 1 is mixed with the reactants and an amine catalyst.

The resulting admixture is coated on a previously primed titanium connector and cured in an oven at 100° C.

The coated connector has a $\gamma_c$ of about 20 dyne/cm and is used in contact with blood to connect a conduit to a left ventricular assist device which is used to treat low cardiac output syndrome.

EXAMPLE 8

A 4 mm tubular prosthesis was formed by coating a stainless steel mandrel with a polymer mixture consisting of 99.8 weight % poly(etherurethane urea) and 0.2 weight % polydimethylsiloxane/polyurethane block copolymer containing 50% polydimethylsiloxane, 50% polyurethane, in a dimethylacetamide solution. After solvent evaporation, the resulting tube was removed from the mandrel, extracted with distilled water at 60° C. for 16 hours, dried and annealed for 4 hours at 60° C. After ethylene oxide sterilization the tube was sutured to the carotid artery of a goat. Using an established radiolabeled platelet technique no enhancement in platelet turnover was measured relative to a sham experiment. A similar experiment easily detects changes in platelet turnover in polyvinylchloride tubing, which is known to have low blood compatibility. The tube treated with the additive according to the invention remains free of blood clots and continues to function as a prosthetic blood vessel for an extended period.

What is claimed is:

1. In a method of forming a thermoplastic modified solid polymer the steps of thoroughly blending a minor portion of a thermoplastic polymer additive throughout a major portion of base polymer, whole said polymer additive and base are in fluid form, to form a polymer admixture, said additive comprising an essentially linear first segmented copolymer chain; said additive characterized by a $\gamma_c$ less than said base polymer and said segmented copolymer characterized by the presence of at least one polar hard segment having a glass transition temperature or crystalline melting temperature above 37° C., and a nonpolar soft block having a glass transition temperature or crystalline melting temperature below 37° C. with the proviso that said base polymer is not a polycarbonate of 4,4'-diphenyldimethylmethane.

2. A method according to claim 1 wherein said additive further comprises a second essentially linear polymer chains chemically bonded to said segmented copolymer chain said second polymer chain being selected from a polar homopolymer or a second segmented polymer, said second segmented copolymer characterized by the presence of at least one polar block segment having a glass transition temperature or crystalline melting temperature above 37° C., and a polar soft block having a glass transition temperature or crystalline melting temperature below 37° C. and solidifying said polymer admixture.

3. The method of claim 2 wherein said nonpolar soft block is characterized by a $\gamma_c$ less than 30 dyne/cm. and a tendency to exude, and said polar hard segments lower, said tendency to exude.

4. In a method of forming a thermoplastic modified solid polymer the steps of thoroughly blending a minor portion of a thermoplastic polymer additive throughout a major portion of a base polymer, while said polymer additive and base polymer are in fluid form, to form a polymer admixture, said additive comprising an essentially linear first segmented copolymer chain; said additive characterized by a $\gamma_c$ less than said base polymer and said segmented copolymer characterized by the presence of at least one polar hard segment having a glass transition temperature or crystalline melting temperature above 37° C., and a nonpolar soft block having a glass transition temperature or crystalline melting temperature below 37° C., wherein said soft blocks control the surface properties of said modified solid polymer, with the proviso that said base polymer is not a polycarbonate of 4,4'-diphenyldimethyl- methane.

5. A method according to claim 4 wherein said additive further comprises a second essentially linear polymer chains chemically bonded to said segmented copolymer chain said second polymer chain being selected from a polar homopolymer or a second segmented polymer, said second segmented copolymer characterized by the presence of at least one polar hard segment having a glass transition temperature or crystalline melting temperature above 37° C., and a polar soft block having a glass transition temperature or crystalline melting temperature below 37° C. and solidifying said polymer admixture.

6. The method of claim 1, 2, 4 or 5 in which the base polymer is selected from the group consisting of a polyurethane, polyester-polyether, polyester, polyether-polyamide, polyamide, styrene-isoprene, styrene-butadiene, thermoplastic polyolefin, styrene-saturated olefin, polyester-polyester, ethylenevinyl acetate, ethylene-ethylacrylate, ionomers, or thermoplastic polydiene.

7. The method of claim 2 or 5 in which said polar soft blocks are independently selected from the group consisting of polyalkylene oxide-copolyalkylene oxides, polyvinylalkanoates and polyalkylene oxides, and said nonpolar soft blocks are selected from the group consisting of polydialkylsiloxanes, polyfluoroalkyl alkylsiloxanes, polyolefins, polydienes and polyfluorocarbons.

8. The method of claim 1, 2, 4 or 5 in which said nonpolar soft block is poly(dimethylsiloxane).

9. The method of claim 1, 2, 4, or 5 in which said segmented copolymer chain comprises a nonpolar soft block of a polydialkylsiloxane, and a polar hard segment of a polyurethane.

10. The method of claim 6 in which said base polymer is a segmented polyurethane.

11. The method of claim 10 in which said base polymer is a reaction product of polymeric ether glycols, a diisocyanate, and a difunctional chain extending agent with active groups selected from the group consisting of amines, hydroxy, and mixtures thereof.

12. The method of claim 1 or 5 in which said base polymer and said polar hard segments of said first and second claims are formed of the same type of homopolymer.

13. The method of claim 1, 2, 4 or 5 further comprising the step of annealing said polymer admixture.

14. The method of claim 1, 2, 4 or 5 in which less than about 2 volume % polymer additive is added to said base polymer based on the total polymer admixture.

15. The method of claim 2 or 5 in which said polymer additive comprises at least about 20 volume % of said homopolymer.

16. The method of claim 2 or 5 in which said polymer additive comprises about 20 to 80 volume % of said polar and nonpolar soft blocks.

17. The method of claim 1, 2, 4 or 5 in which said polymer additive comprises about 80 to 20 volume % of said polar hard segments.

18. The method according to claim 6 wherein said base polymer is a thermoplastic polyolefin admixed with plasticizers.

19. The method according to claim 6 wherein said base polymer is polyvinyl chloride.

20. The method of claim 1, 2, 4 or 5 in which said polymer admixture is deposited as a film onto a biomedical device or component thereof.

21. The method of claim 1, 2, 4 or 5 in which said additive and base polymer are in molten form during dispersion and solidify on cooling.

22. The method of claim 1, 2, 4 or 5 in which said polymer admixture is dissolved in solvent during mixing and said solvent is removed to solidify said polymer mixture.

23. The method of claim 1, 2, 4 or 5 in which said base polymer comprises a curable thermosetting fluid polymer which is solidified by curing.

24. The method of claim 1, 2, 4 or 5 in which said modified solid polymer is formed into an exposed blood and tissue-contacting surface of a biomedical device, or component thereof.

25. The method according to claim 24 wherein said surface comprises fibers.

26. The method according 1, 2, 4 or 5 wherein said modified solid polymer is formed into a textile or component of the same.

27. The method of claim 1, 2, 4 or 5 in which no greater than about 5 volume % of said polymer additive is dispersed in at least 95% of said base polymer.

28. In a method of forming a polymer admixture, the steps of
(a) thoroughly dispersing no greater than about 5 volume % of a copolymer additive throughout at least 95 volume % of a base polymer, while said copolymer additive and base polymer are in fluid form, to form a polymer admixture, said copolymer additive comprising a nonpolar soft poly (dialkysiloxane) segment component chemically bonded to a polar hard polyurethane segment, said copolymer additive being characterized by a $\gamma_c$ less than said base polymer admixture being characterized by a $\gamma_c$ between about 10 and 35 dyne/cm., and
(b) solidifying said polymer admixture.

29. A biomedical device or component of the same, including a blood-compatible, blood-contacting surface formed of a polymer admixture comprising at least 95 volume % of a base polymer and no greater than 5 volume % of a polymer additive comprising a first homopolymer component chemically bonded to at least a second homopolymer component of a different type than said first component, said polymer additive being dispersed throughout said base polymer and being characterized by a $\gamma_c$ less than said base polymer, said polymer admixture being characterized by a $\gamma_c$ between about 10 and 35 dyne/cm.

30. The biomedical device of claim 29 in which said first component is characterized by a $\gamma_c$ less than 30 dyne/cm. and a tendency to exude, and said second component lowers said tendency to exude.

31. The biomedical device of claim 29 in which said first component is a homopolymer selected from the group consisting of polydialkylsiloxanes, polyfluoroalkyl alkylsiloxanes, polyalkylene oxides, polyolefins, polydienes and polyfluorocarbons.

32. The biomedical device of claim 29 in which said first component is poly(dimethylsiloxane).

33. The biomedical device of claim 29 in which said first component is a polydialkylsiloxane and said second component is a polyurethane.

34. The biomedical device of claim 29 characterized by blood compatibility in the form of a blood contact device or component thereof.

35. The biomedical device of claim 29 characterized by blood compatibility in the form of a blood contact layer adhered to the surface of a blood contact device.

36. The biomedical device of claim 29 in which a portion of said polymer additive is in the form of a continuous layer on the surface of a blood contact device.

37. The biomedical device of claim 29 in which a portion of said polymer additive comprises a linear multiblock copolymer with blocks of at least said first and second component on the surface of a blood contact device.

38. The biomedical device of claim 29 in which a portion of said polymer additive comprises a graft copolymer with a substrate formed of said first component and pendant chains formed of said second component on the surface of a blood contact device.

39. The biomedical device of claim 29 in which a portion of said polymer additive comprises a graft copolymer with a substrate formed of said second component and pendant chains formed of said first component on the surface of a blood contact device.

40. A modified solid polymer blend formed of a base polymer and a solid thermoplastic segmented block copolymer additive blended with said base polymer,
    said additive comprising a first essentially linear segmented copolymer chain and a second essentially linear polymer chain chemically bonded to said segmented copolymer chain, said second polymer chain comprising a polar homopolymer;
    said additive characterized by $\gamma_c$ less than said base polymer and said first segmented copolymer chain characterized by the presence of at least one polar hard segment having a glass transition temperature or crystalline melting temperature above 37° C., and a nonpolar soft block having a glass transition temperature or crystalline melting temperature below 37° C.;
    said polar homopolymer characterized by the presence of at least one second polar hard segment having a glass transition temperature or crystalline melting temperature above 37° C., said polar hard segments independently selected from the group consisting of a polyurethane and polycarbonate of 4,4'-diphenylmethylmethane, wherein said nonpolar and polar soft blocks control the surface properties of said modified solid polymer blend.

41. A modified, solid polymer and a solid thermoplastic segmented block copolymer additive blended with said base polymer,
    said additive comprising an essentially linear segmented copolymer chain; said additive characterized by $\gamma_c$ less than said base polymer and said segmented copolymer chain characterized by the presence of at least one polar hard segment having a glass transition temperature or crystalline melting temperature above 37° C., and a nonpolar soft block having a glass transition temperature below 37° C. said additive further comprising a second essentially linear polymer chain chemically bonded to said segmented copolymer chain, said second polymer chain selected from a polar homopolymer or a second segmented copolymer, said second segmented copolymer or polar homopolymer characterized by the presence of at least one second polar hard segment having a glass transition temperature or crystalline melting temperature above 37° C., said polar hard segments independently selected from the group consisting of a polyurethane and a polyurethaneurea, and said second segmented copolymer further characterized by the presence of a polar soft block having a glass transition temperature or crystalline melting temperature below 37° C. with the proviso that said base polymer is not a polycarbonate of 4,4'-diphenyldimethylmethane; and wherein said base polymer and said polar hard segments are formed of the same type of homopolymer.

42. A method of forming an exposed blood-contacting surface of biomedical device or component thereof of low surface free energy and increased contact angle hysteresis comprising the steps of
    (a) reacting up to about 2 volume % of a reactive polysiloxane oligomer with at least 98 volume % of a base polymer, while said oligomer and base polymer are in fluid from to form a fluid polymer admixture of at least 95 volume % pure base polymer and no greater than 5 volume % of a copolymer of said base polymer and said oligomer, and
    (b) solidifying said polymer admixture, said copolymer comprising an essentially linear segmented copolymer chain; said copolymer characterized by a $\gamma_c$ less than said base polymer and said segmented chain characterized by the presence of at least one polar hard polyurethane or polyurethaneurea segment having a glass transition temperature or crystalline melting temperature above 37° C., and a nonpolar polysiloxane soft block having a glass transition temperature or crystalline melting temperature below 37° C. with the proviso that said base polymer is not a polycarbonate of 4,4'-diphenyldimethylmethane and said polymer admixture being characterized by a $\gamma_c$ between about 10 and 35 dyne/cm.

43. The method according to claim 42 wherein said surface comprises fibers.

44. The method of claim 42 in which said polymer admixture is formed into a textile or component thereof.

45. In method of forming the exposed blood-contacting surface of a biomedical device, or components thereof, the steps of
    (a) thoroughly dispersing no greater than about 5 volume % of a polymer additive throughout at least 95 volume % of a base polymer, while said polymer additive and base polymer are in fluid form, to form a polymer admixture, said polymer additive comprising a thermoplastic segmented block copolymer characterized by the presence of at least one polar hard segment of from 1 to 10 repeating monomer units, said segment selected from the group consisting of a polyurethane and a polyurethaneurea and having a glass transition temperature or crystalline melting temperature above 37° C. and a nonpolar soft block having a glass transition temperature or a crystalline melting temperature below 37° C., said polymer additive being characterized by a $\gamma_c$ between about 10 and 35 dyne/cm; and
    (b) solidifying said polymer mixture and
    (c) depositing said polymer mixture as a film onto a biomedical device or component thereof.

46. The method of claim 45 which said additive and base polymer are in molten form during dispersion and solidify on cooling.

47. The method of claim 45 in which said polymer admixture is dissolved in solvent during mixing and said solvent is removed to solidify said polymer admixture.

48. The method of claim 45 said base polymer comprises a curable thermosetting fluid polymer which is solidified by curing.

49. A polymeric blood-contacting surface of a biomedical device or component thereof comprising at least 95 volume % of a base polymer and no greater than 5 volume % of a solid polymer additive comprising a poly(dialkysiloxane) block chemically bonded to a polyurethane segment of from 1 to 10 repeating monomer units said polymer additive being dispersed throughout said base polymer and being characterized by a $\gamma_c$ less than said base polymer, said polymer admixture being characterized by a $\gamma_c$ between about 10 and 35 dyne/cm.

50. A modified solid polymer blend formed of a base polymer including end groups capable of hydrogen bonding or reacting with proteins and a solid thermoplastic segmented block copolymer additive blended with said base polymer, said additive comprising a first essentially linear segmented copolymer chain and a second essentially linear polymer chain chemically bonded to said first segmented copolymer chain, said second polymer chain being selected from a polar homopolymer or a second segmented copolymer said additive characterized by a $\gamma_c$ less than said base polymer and said first segmented copolymer chain characterized by the presence of at least one polar hard segment having a glass transition temperature or crystalline melting temperature above 37° C., and a nonpolar soft block having a glass transition temperature or crystalline melting temperature below 37° C.;

said second segmented copolymer or polar homopolymer characterized by the presence of at least one second polar hard segment having a glass transition temperature or crystalline melting temperature above 37° C., and said second segmented copolymer further characterized by the presence of a polar soft block having a glass transition temperature or crystalline melting temperatures below 37° C., said polar hard segments independently selected from the group consisting of a polyurethane and a polyurethaneura wherein said nonpolar and polar soft blocks control the surface properties of said modified solid polymer blend; and said base is selected from the group consisting of a polyurethane, polyester, polyesterether, polyamide, polyether-polyamide, styrene-isoprene, styrene-butadiene, thermoplastic polyolefin, styrene-saturated olefin, polyester-polyester, ethylenevinyl acetate, ethylene-ethylacrylate, ionomers and thermoplastic polydiene.

51. A modified, solid polymer formed of a base polymer including end groups capable of hydrogen bonding or reacting with proteins and a solid thermoplastic segmented block copolymer additive blended with said base polymer, said additive comprising an essentially linear segmented copolymer chain; said additive characterized by $\gamma_c$ less than said base polymer and said segmented copolymer chain characterized by the presence of at least one polar hard segment having a glass transition temperature of crystalline melting temperature above 37° C., and a nonpolar soft block having a glass transition temperature below 37° C. said additive further comprising a second essentially linear polymer chain chemically bonded to said segmented copolymer chain, said second polymer chain being selected from a polar homopolymer or a second segmented copolymer, said second segmented copolymer or polar homopolymer characterized by the presence of at least one second polar hard segment having a glass transition temperature or crystalline melting temperature above 37° C., said polar hard segments independently selected from the group consisting of a polyurethane and a polyurethaneurea, and said second segmented copolymer further characterized by the presence of polar soft block having a glass transition temperature or crystalline melting temperature below 37° C.; and said base polymer is selected from the group consisting of a polyurethane, polyester, polyesterpolyether, polyamide, polyether-polyamide, styrene-isoprene, styrene-butadiene, thermoplastic polyolefin, styrene-saturated olefin, polyester-polyester, ethylene-vinyl acetate, ethylethylacrylate, ionomers, and thermoplastic polydiene.

52. A modified solid polymer blend formed of a base polymer comprising a segmented block polymer and a solid thermoplastic segmented block copolymer additive blended with said base polymer, said additive comprising a first essentially linear segmented copolymer chain and a second essentially linear polymer chain chemically bonded to said first segmented copolymer chain, said second polymer chain being selected from a polar homopolymer or a second segmented copolymer said additive characterized by a $\gamma_c$ less than said base polymer and said first segmented copolymer chain characterized by the presence of at least one polar hard segment having a glass transition temperatures or crystalline melting temperature above 37° C., and a nonpolar soft block having a glass transition temperature or crystalline melting temperature below 37° C.;

said second segmented copolymer or polar homopolymer characterized by the presence of at least one second polar hard segment having a glass transition temperature or crystalline melting temperature above 37° C., and second segmented copolymer further characterized by the presence of a polar soft block having a glass transition temperature or crystalline melting temperature below 37° C., said polar hard segments independently selected from the group of a polyurethane and a polyurethaneurea wherein said nonpolar and polar soft blocks control the surface properties of said modified solid polymer blend; and said base polymer is selected from the group consisting of a polyurethane, polyester, polyesterpolyether, polyamide, polyether-polyamide, styrene-isoprene, styrene-butadiene, thermoplastic polyolefin, styrene-saturated olefin, polyesterpolyester, ethylenevinyl acetate, ethylene-ethylacrylate, ionomers and thermoplastic polydiene.

53. A modified, solid polymer formed of a base polymer comprising a segmented block copolymer and a solid thermoplastic segmented block copolymer additive blended with said base polymer, said additive comprising an essentially linear segmented copolymer chain; said additive characterized by a $\gamma_c$ less than said base polymer and said segmented copolymer chain characterized by the presence of at least one polar hard segment having a transition temperature or crystalline melting temperature above 37° C., and a nonpolar soft block having a glass transition temperature below 37° C.

said additive chemically bonded to said segmented copolymer chain, said second polymer chain being selected from a polar homopolymer or a second segmented copolymer, said second segmented copolymer or polar homopolymer characterized by the presence of at least one second polar hard segment having a glass transition temperature or crystalline melting temperature 37° C., said polar hard segments independently selected from the group consisting of a polyurethane and a polyurethaneurea, and said second segmented copolymer further characterized by the presence of a polar soft block having a glass transition temperature or crystalline melting temperature below 37° C.; and said base polymer is selected from the group consisting of a polyurethane, polyester, polyester-polyether, polyamide, polyether-polyamide, styrene-isoprene, styrene-butadiene, thermoplastic polyolefin, styrene, saturated olefin, polyester-polyester, ethylene-vinyl acetate, ethylethylacrylate, ionomers, and thermoplastic polydiene.

54. A modified solid polymer blend formed of a segmented polyurethane base polymer and a solid thermoplastic segmented block copolymer additive blended with said base polymer, said additive comprising a first essentially linear segmented copolymer chain and a second essentially linear polymer chain chemically bonded to said first segmented copolymer chain, said second polymer chain being selected from a polar homopolymer or a second segmented copolymer said additive characterized by a $\gamma_c$ less than base polymer and said first segmented copolymer chain characterized by the presence of at least one polar hard segment having a glass transition temperature or crystalline melting temperature above 37° C., and a nonpolar soft block having a glass transition temperature or crystalline melting temperature below 37° C.;

said second segmented copolymer or polar homopolymer characterized by the presence of at least one second polar hard segment having a glass transition temperature or crystalline melting temperature above 37° C., and said second segmented copolymer further characterized by the presence of a polar soft block having a glass transition temperature or crystalline melting temperature below 37° C., said polar hard segments independently selected from the group consisting of a polyurethane and a polyurethaneurea with the proviso that said base polymer is not a polycarbonate of 4,4′-diphenylmethylmethane, wherein said nonpolar and polar soft blocks control the surface properties of said modified solid polymer blend.

55. A modified solid polymer according to claim 54 wherein said segmented polyurethane is a reaction product of polymeric ether glycols, a diisocyanate, and a disfunctional chain extending agent with active groups selected from the group consisting of amines, hydroxy, and mixtures thereof.

56. A modified, solid polymer formed of a segmented polyurethane base polymer and a solid thermoplastic segmented block copolymer additive blended with said base polymer, said additive comprising an essentially linear segmented copolymer chain; said additive characterized by $\gamma_c$ less than said base polymer and said segmented copolymer chain characterized by the presence of at least one polar hard segment having a glass transition temperature or crystalline melting temperature above 37° C., and a nonpolar soft block having a glass transition temperature below 37° C. said additive further comprising a second essentially linear polymer chain chemically bonded to said segmented from a polar homopolymer or a second segmented copolymer, said second segmented copolymer or polar homopolymer characterized by the presence of at least one second polar hard segment having a glass transition temperature or crystalline melting temperature above 37° C., polar hard segments independently selected from the group consisting of a polyurethane and a polyurethaneurea, and said second segmented copolymer further characterized by the presence of a polar soft block having a glass transition temperature or crystalline melting temperature below 37° C. with the proviso that said base polymer is not a polycarbonate of 4,4′-diphenyldimethylmethane.

57. A modified solid polymer according to claim 56 wherein said segmented polyurethane is a reaction product of polymeric ether glycols, a diisocyanate, and a difunctional chain extending agent with active groups selected from the group consisting of amines, hydroxy, and mixtures thereof.

58. A modified solid polymer formed of a bas polymer formed of a homopolymer and characterized by a glass transition temperature below 140° C. and a thermoplastic segmented block copolymer additive blended with said base polymer, said additive comprising an essentially linear segmented copolymer chain; said additive characterized by $\gamma_c$ less than said base polymer and said segmented copolymer chain characterized by the presence of at least one polar hard segment formed of said same homopolymer comprising said base polymer and having a glass transition temperature or crystalline melting temperature above 37° C., and a nonpolar soft block having a glass transition temperature or crystalline melting temperature below 37° C. with the proviso that said base polymer is not a polycarbonate of 4,4′-diphenyldimethylmethane.

59. A modified solid formed of a base formed of a homopolymer, and a thermoplastic segmented block copolymer additive blended with said base polymer said modified solid polymer characterized by a relative contact angle hysteresis greater than that of said base polymer, said additive comprising an essentially linear segmented copolymer chain; said additive characterized by a $\gamma_c$ less than said base polymer and said segmented copolymer chain characterized by the presence of at least one polar hard segment formed of said same homopolymer comprising said base polymer and having a glass transition temperature or crystalline melting temperature above 37° C., and a nonpolar soft block having a glass transition temperature or crystalline melting temperature below 37° C. with the proviso that said base polymer is not a polycarbonate of 4,4′-diphenyldimethylmethane.

60. A modified solid polymer formed of a base polymer formed of a homopolymer, and a thermoplastic segmented block copolymer additive blended with said base polymer, said additive comprising an essentially linear segmented copolymer chain; said additive characterized by a $\gamma_c$ less than said base polymer and said segmented copolymer chain characterized by the presence of at least one polar hard segment formed of said same homopolymer comprising said base polymer and having a glass transition temperature or crystalline melting temperature above 37° C., and a nonpolar soft block having a glass transition temperature or crystalline melting temperature below 37° C. with the proviso that said base polymer is not a polycarbonate of 4,4'-diphenyldimethylmethane; wherein said soft blocks control the surface properties of said modified solid polymer.

61. A blood-contacting surface of a biomedical device or component of said device comprising a polymer admixture of low surface free energy, said admixture formed by (a) reacting about 0.0002 to 2 volume % of a homopolymer additive with at least 98 volume % of a base polymer, while said homopolymer additive and base polymer are in fluid form to form a fluid polymer admixture of at least 95 volume % pure base polymer and no greater than 5 volume % of a copolymer of said base polymer and said homopolymer additive, and solidifying said polymer admixture, said additive polymer being characterized by a $\gamma_c$ less than said base polymer and said polymer admixture being characterized by a $\gamma_c$ between about 10 and 35 dyne/cm.

* * * * *